US00PP23953P2

(12) United States Plant Patent
Kordes

(10) Patent No.: US PP23,953 P2
(45) Date of Patent: Oct. 8, 2013

(54) MINATURE ROSE PLANT NAMED 'KORPOT020'

(50) Latin Name: *Rosa hybrida*
Varietal Denomination: KORpot020

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 89 days.

(21) Appl. No.: 13/385,491

(22) Filed: Feb. 21, 2012

(51) Int. Cl.
*A01H 5/00* (2006.01)

(52) U.S. Cl.
USPC ..... Plt./119

(58) Field of Classification Search
USPC ..... Plt./119
See application file for complete search history.

(56) References Cited

U.S. PATENT DOCUMENTS

PP6,808 P * 5/1989 Saville ..... Plt./119
PP15,044 P2 * 7/2004 Olesen et al. ..... Plt./119

* cited by examiner

*Primary Examiner* — Wendy C Haas

(57) ABSTRACT

A new and distinct variety of rose with long lasting, novel orange-red flowers, with attractive foliage with good disease resistance. It exhibits moderate growth and a compact, upright habit. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORpot020'. The new variety of rose plant of the present invention originated from a controlled crossing in a breeding program of two distinct parents during the summer of 2008. The crossing was between an 'unnamed seedling' and an 'unnamed seedling'.

The resulting seeds were planted in glasshouse benches during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot020'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an unnamed seedling, by the following combination of characteristics:

1. The flower size of 'KORpot020' is medium while the flower size of the seed parent is large.
2. The petal count of 'KORpot020' is double while the petal count of the seed parent is semi-double.

The new rose plant may be distinguished from its pollen parent, an 'un-named seedling' by the following combination of characteristics:

1. The bud form of 'KORpot020' is a long pointed ovoid while the bud form of the pollen parent is globular.
2. The petal count of 'KORpot020' is double while the petal count of the pollen parent is very double.

The objective of the hybridization was to create a new and distinct rose plant with unique qualities, such as:

1. Uniform growth and flowering;
2. Abundant attractive orange-red, recurrent flowers;
3. Attractive and abundant foliage; and
3. Excellent shelf life when grown as a floral pot rose.

This combination of qualities is not present in prior rose cultivars known to the inventor. These objectives have been substantially achieved and in that distinguish 'KORpot020' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot020' was selected in May 2009 from the seedling beds to be asexually propagated for further evaluation. The first asexual propagation of 'KORpot020' was done by rooting softwood cuttings in June, 2009 at the inventor's nursery in Offenseth-Sparrieshoop, Germany.

This initial and other subsequent propagations conducted in controlled environments demonstrate that 'KORpot020' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot020'.

DETAILED BOTANICAL DESCRIPTION

The following is a description of 'KORpot020', as observed growing in October, 2011 in a nursery in Jackson County, Oreg. on plants of 6 months years of age. Color references are made using The Royal Horticultural Society (London, England) Colour Chart, 2001 except where common terms of color are used.

For a comparison, several physical characteristics of the rose variety 'KORoragut', a rose variety from the same inventor described and illustrated in U.S. Plant Pat. No. 14,982 and issued on Jul. 6, 2004 are compared to 'KORKORpot020' in Chart 1.

CHART 1

| Characteristic | 'KORpot020' | 'KORoragut' |
|---|---|---|
| Flower Diameter | 50 mm | 50-55 mm |
| Petal Count | Approximately 18 | 50-60 |
| General Tonality of open flower | Orange-Red Group 33C | Red Group 40A |

Parents:

*Seed parent.*—'Unnamed seedling'.

*Pollen parent.*—'Unnamed seedling'.

Classification:

*Botanical classification.*—*Rosa hybrida* 'KORpot020'.

*Commercial classification.*—Miniature rose.

FLOWER AND FLOWER BUD

Blooming habit: Recurrent.

Flower bud:

*Size.*—Upon opening, 20 mm in length from base of receptacle to distal end of bud and 12 mm diameter at its widest point.

*Bud form.*—Long, pointed ovoid.

*Bud color.*—As sepals first unfold, bud color is Red Group 45A. When ¼ open, the upper surface of petals is Red Group 42B, and the lower surface is Orange-Red Group 33B.

*Sepals.*—Color: Upper surface Yellow-Green Group 146D. Lower surface Yellow-Green Group 14B. Size: Average 23-30 mm (l)×3-5 mm (w). Shape: Strong foliaceous appendages on 2 of the 5 sepals. Apex: Apiculate on 3 sepals and cirrose on 2 sepals. Base: Flat at union with receptacle.

*Quantity.*—Five.

*Surface texture.*—Upper side: Pubescent. Lower surface: Pubescent.

*Margins.*—Pubescent with stipitate glands.

Receptacle:

*Surface.*—Smooth.

*Color.*—Yellow-Green Group 146C.

*Shape.*—Funnel-shaped.

*Size.*—8 mm (h)×4 mm (w).

Peduncle:

*Surface.*—Generally smooth with occasional stipitate glands.

*Length.*—40 to 50 mm average length.

*Diameter.*—1.5 to 2 mm average diameter.

*Color.*—Yellow-Green Group 146C.

*Strength.*—Moderately strong.

*Borne.*—Singly.

Flower bloom:

*Fragrance.*—None.

*Duration.*—On the plant 12 to 15 days. Long lasting. As a cut flower, 7 to 8 days. Senesced petals clinging.

*Size.*—Medium sized for a miniature rose. When open, the average flower diameter is 50 mm and the average flower height is 15 mm.

*Form.*—Shape of flower when viewed from the side: Upon opening, upper part: Flat. Upon opening, lower part: Flat. Open flower, upper part: Flattened convex. Open flower, lower part: Concave.

Color:

*Upon opening, petals.*—Outermost petals: Outer Side: Red Group 46C. Inner Side: Orange-Red Group 34C. Innermost petals: Outer Side: Red Group 43A. Inner Side: Orange-Red Group 30B.

*Upon opening, basal petal spots.*—Basal petal spot, outermost petals: Outer Side: Yellow Group 4A. Inner Side: Yellow Group 2B. Basal petal spot, innermost petals: Outer Side: Yellow Group 3A. Inner Side: Yellow Group 2B.

*After opening, petals.*—Outermost petals: Outer Side: Red Group 46C. Inner Side: Orange-Red Group 33C. Innermost petals: Outer Side: Red Group 43A. Inner Side: Orange-Red Group 30B.

*After opening, basal petal spots.*—Basal petal spot, outermost petals: Outer Side: Green-Yellow Group 1C. Inner Side: Yellow Group 2B. Basal petal spot, innermost petals: Outer Side: Red Group 44C. Inner Side: Orange-Red Group 32C.

General tonality: On open flower Orange-Red Group 33C. No change in the general tonality at the end of the 7th day. Afterwards, general tonality is Red Group 38A.

Petals:

*Petal count.*—Semi-double. Average is approximately 18 petals under normal conditions.

*Petal reflex.*—Petals reflex strongly.

*Petal edge.*—Entire.

*Petal shape.*—Obovate. Apex shape is obtuse. Shape of base is obtuse.

*Petal size.*—15 to 25 mm (l) 15 to 25 mm (w).

*Thickness.*—Thin.

*Petal arrangement.*—Formal.

Petaloids:

*Petaloid count.*—Average of 3 to 5 per flower.

*Petaloid size.*—Petaloids are 5 to 15 mm (l) and 3 to 8 mm (w).

*Petaloid color.*—Color of inner side is Orange-Red Group 32C. Color of outer side is Red Group 44C.

*Petaloid texture.*—Average.

*Margins.*—Undulated.

*Petaloid shape.*—Oblanceolate. Apex: Obtuse to irregular. Base: Attenuate.

Reproductive organs:

*Pistils.*—Approximately 14 to 18 present. Stigmas: Location: Slightly inferior in position to anthers. Color: Greyed-Red Group 182B. Styles: Length: About 3 mm long. Color: Greyed-Orange Group 176B.

*Stamens.*—Approximately 30 to 40 on average and regularly arranged. Anthers: Size: About 1 mm long. Pollen: Generally present. Color: Greyed-Orange Group 163C. Filaments: Color: Yellow-Orange Group 15C. Length: About 5 to 6 mm.

THE PLANT

Growth: Moderately vigorous.

Plant habit: Compact and upright habit. When grown as 13 cm container plant the average plant height is 30 cm and the average plant width is 20 cm.

Stems:

*Stem color.*—Juvenile wood: Yellow-Green Group 144B. Mature wood: Yellow-Green Group 146B.

*Stem surface.*—Juvenile wood: Smooth. Mature wood: Smooth.

Prickles: Present.

*Incidence.*—Average of 2 to 3 per each 10 cm of stem.

*Size.*—Average length: 3 to 5 mm.

*Color.*—Immature prickles: Green-Yellow Group 1C. Mature prickles: Green-Yellow Group 1C. Senescing to Greyed-Brown Group 199A.

*Shape.*—Linear.

Leaves and leaflets: Normally 5 leaflets on normal leaves in middle of the stem.

*Venation pattern.*—Pyramidal net pattern.

*Leaf size.*—Average 90 mm (l)×65 mm (w).

*Abundance.*—Average.

*Texture.*—Thin. Upper side of leaflet: Semi-glossy and smooth. Under side of leaflet: Matte and smooth.

*Color, mature foliage.*—Upper Leaf Surface: Green Group 137A. Lower Leaf Surface: Green Group 138B.

*Color, juvenile foliage.*—Upper Leaf Surface: Yellow-Green Group 146A. Lower Leaf Surface: Yellow-Green Group 146C.

*Anthocyanin intonation.*—Present. Intonations present Upper and lower surfaces of juvenile foliage.

Stipules:

*Size.*—12 mm long, 3 mm from distal tip to distal tip.

*Stipule color.*—Yellow-Green Group 144A.

*Stipitate glands.*—Present on upper side and margins.

*Shape.*—Apex: Apiculate. Base: Flat.

Petiole:

*Length.*—Average 16 mm.

*Diameter.*—Average 1 mm.

*Petiole color.*—Yellow-Green Group 144A.

*Underneath.*—Generally smooth with occasional stipitate glands.

*Margins.*—With stipitate glands.

Petiole rachis:

*Length.*—Average 15 mm.

*Diameter.*—Average 1 mm.

*Color.*—Yellow-Green Group 144A.

*Margins.*—With stipitate glands.

*Prickles.*—Lacking.

*Stipitate glands.*—Lacking.

Leaflets:

*Size.*—Average size of the terminal leaflet is 40 mm (l)×20 mm (w).

*Shape.*—Ovate. Base: Obtuse. Apex: Acute.

*Margins.*—Serrated.

*Surface.*—Upper: Semi-glossy. Lower: Matte.

*Texture.*—Thin.

*Arrangement.*—Odd pinnate.

*Venation.*—Reticulate.

Hips/seed formation: None observed.

Winter hardiness: To date, the variety has been grown successfully in USDA Zones 5-9.

Disease resistance: Good resistance to Powdery mildew (*Sphaerotheca pannosa*) and *Botrytis* (*Botrytis cinerea*) diseases under normal growing conditions.

I claim:

1. A new and distinct variety of rose plant, as described and illustrated herein.

* * * * *

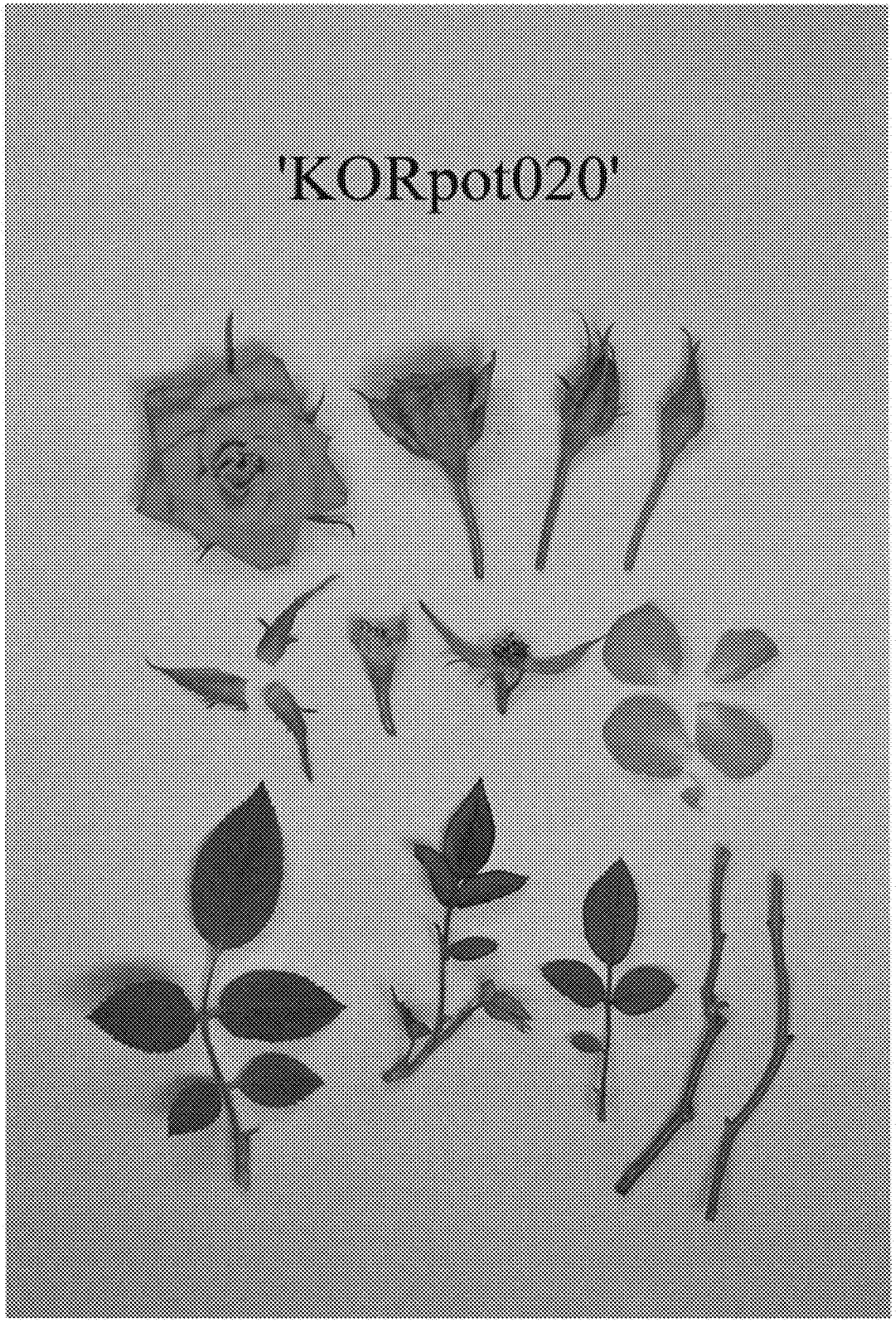
'KORpot020'